United States Patent
Murray et al.

(10) Patent No.: US 9,040,031 B2
(45) Date of Patent: May 26, 2015

(54) HAIR CARE COMPOSITION

(75) Inventors: Andrew Malcolm Murray, Wirral (GB); Thuy-Anh Pham, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 176 days.

(21) Appl. No.: 13/805,365

(22) PCT Filed: Jun. 22, 2011

(86) PCT No.: PCT/EP2011/060419
§ 371 (c)(1),
(2), (4) Date: Dec. 19, 2012

(87) PCT Pub. No.: WO2012/004126
PCT Pub. Date: Jan. 12, 2012

(65) Prior Publication Data
US 2013/0095056 A1    Apr. 18, 2013

(30) Foreign Application Priority Data
Jul. 8, 2010    (EP) .................... 10168898

(51) Int. Cl.
| A61K 8/92 | (2006.01) |
| A61K 8/34 | (2006.01) |
| A61K 8/41 | (2006.01) |
| A61K 8/44 | (2006.01) |
| A61K 8/46 | (2006.01) |
| A61K 8/73 | (2006.01) |
| A61Q 5/02 | (2006.01) |
| A61Q 5/12 | (2006.01) |
| A61Q 19/00 | (2006.01) |
| A61Q 5/00 | (2006.01) |

(52) U.S. Cl.
CPC . *A61K 8/92* (2013.01); *A61K 8/342* (2013.01); *A61K 8/416* (2013.01); *A61K 8/44* (2013.01); *A61K 8/463* (2013.01); *A61K 8/737* (2013.01); *A61Q 5/02* (2013.01); *A61Q 5/12* (2013.01); *A61Q 19/00* (2013.01); *A61Q 5/00* (2013.01)

(58) Field of Classification Search
None
See application file for complete search history.

(56) References Cited

U.S. PATENT DOCUMENTS

| 932,610 | A | 8/1909 | Hodgson |
| 3,932,610 | A | 1/1976 | Rudy et al. |
| 3,950,510 | A | 4/1976 | Adams |
| 3,957,971 | A | 5/1976 | Oleniacz |
| 3,958,581 | A | 5/1976 | Abegg |
| 3,962,418 | A | 6/1976 | Birkofer |
| 3,964,500 | A | 6/1976 | Drakoff |
| 4,009,256 | A | 2/1977 | Nowak |
| 4,942,038 | A | 7/1990 | Wallach |
| 5,194,639 | A | 3/1993 | Connor |
| 5,393,521 | A | 2/1995 | Lance-Gomez |
| 5,683,683 | A | 11/1997 | Scafidi |
| 5,892,116 | A | 4/1999 | Weiss et al. |
| 5,990,059 | A | 11/1999 | Finel |
| 6,248,315 | B1 | 6/2001 | Young |
| 6,582,685 | B1 | 6/2003 | Adams et al. |
| 7,303,744 | B2 | 12/2007 | Wells et al. |
| 8,236,290 | B2 | 8/2012 | Bjornberg et al. |
| 2001/0008631 | A1 | 7/2001 | Ellis |
| 2001/0056049 | A1 | 12/2001 | Aronson |
| 2002/0085987 | A1 | 7/2002 | Brown et al. |
| 2002/0119113 | A1 | 8/2002 | Ellis |
| 2002/0119906 | A1 | 8/2002 | Smith |
| 2002/0122772 | A1 | 9/2002 | Lukenbach |
| 2003/0007945 | A1 | 1/2003 | Arif |
| 2003/0134760 | A1 | 7/2003 | Harrison |
| 2003/0215479 | A1 | 11/2003 | Sendelbach |
| 2003/0223952 | A1 | 12/2003 | Wells et al. |
| 2003/0228334 | A1 | 12/2003 | Mercier et al. |
| 2004/0105831 | A1 | 6/2004 | Frantz |
| 2004/0223929 | A1 | 11/2004 | Clapp et al. |
| 2005/0043194 | A1 | 2/2005 | Macaulay |
| 2005/0123487 | A1 | 6/2005 | Spadini et al. |
| 2006/0024256 | A1 | 2/2006 | Wells et al. |
| 2006/0083704 | A1 | 4/2006 | Torgerson |
| 2006/0094628 | A1 | 5/2006 | Wei |
| 2006/0105933 | A1 | 5/2006 | Hayashi |
| 2006/0160713 | A1 | 7/2006 | Sekine |
| 2006/0269501 | A1 | 11/2006 | Johnson et al. |
| 2006/0269502 | A1 | 11/2006 | Johnson et al. |
| 2007/0015443 | A1 | 1/2007 | Moore |

(Continued)

FOREIGN PATENT DOCUMENTS

| CN | 1658830 | 8/2005 |
| CN | 1784201 | 6/2006 |

(Continued)

OTHER PUBLICATIONS

What is the zero shear viscosity, wiki.answers.com, May 23, 2013, 1-2, , US.

Masalci et al., "Compared properties of textures of lyotropic mesophases of binary and ternary systems based on tetradecyltrimethyl", Journal of Molecular Structure, 2009, vol. 919, pp. 1-6.

Ramaraju et al., "The liquid crystalline phaes formed by linear-dodecylbenzene sulphonic acid during neutralisation with sodium carbonate", Colloids and Surfaces A: Physicochem. Eng. Aspects, Apr. 7, 2006, vol. 288, pp. 77-85.

Richard et al., "Liquid crystal and solution phases of sodium dodecyl-p-benzene sulfonate (LAS) and hexa-oxyethylene glycol dodecyl ether (C12E6); 1:1 mixtures in water", Colloids and Surfaces A: Physicochemical Engeering Aspects, 2006, vol. 288, pp. 103-112.

*Primary Examiner* — H. Sarah Park
(74) *Attorney, Agent, or Firm* — Ronald A. Koatz

(57) ABSTRACT

A personal care composition comprising: i) a cleaning phase comprising a cleansing anionic surfactant which is a salt and comprises an alkyl group with from 8 to 14 carbons; ii) an aqueous conditioning gel network having no overall charge or being anionic, the gel network comprising: (a) fatty material; (b) a gel network anionic surfactant comprising an alkyl group with from 16 to 30 carbons; (c) cationic surfactant; (d) an active material selected from fragrances, vitamins, sunscreens and cooling agents; and iii) a cationic deposition polymer.

8 Claims, No Drawings

(56) References Cited

U.S. PATENT DOCUMENTS

| | | |
|---|---|---|
| 2007/0110696 A1 | 5/2007 | Johnson |
| 2007/0110700 A1 | 5/2007 | Wells et al. |
| 2008/0008668 A1 | 1/2008 | Harichian et al. |
| 2008/0139434 A1 | 6/2008 | Basappa |
| 2008/0187507 A1 | 8/2008 | Johnson et al. |
| 2009/0010866 A1 | 1/2009 | Avery |
| 2009/0233825 A1 | 9/2009 | Giles |
| 2009/0325012 A1 | 12/2009 | Nor |
| 2010/0149460 A1 | 6/2010 | Akao |
| 2011/0212043 A1 | 9/2011 | Pham |
| 2011/0212879 A1 | 9/2011 | Madden |
| 2012/0087883 A1 | 4/2012 | Leray |

FOREIGN PATENT DOCUMENTS

| | | |
|---|---|---|
| CN | 101005826 | 7/2007 |
| CN | 101005826 A | 7/2007 |
| EP | 0170927 A2 | 2/1986 |
| EP | 0584692 | 3/1994 |
| EP | 0902008 | 3/1999 |
| EP | 1250938 | 10/2002 |
| EP | 1714678 | 10/2006 |
| EP | 1778180 | 5/2007 |
| EP | 1859777 | 11/2007 |
| FR | 2262106 | 9/1975 |
| GB | 1419117 | 12/1975 |
| GB | 1425939 A | 2/1976 |
| GB | 1426727 | 3/1976 |
| GB | 2280682 | 8/1995 |
| JP | S48062950 | 9/1973 |
| JP | 10293210 | 11/1998 |
| JP | 11512388 | 10/1999 |
| JP | 2001503439 | 3/2001 |
| JP | 2004503570 | 2/2004 |
| JP | 2004503570 A | 2/2004 |
| JP | 2004292387 | 10/2004 |
| JP | 2007204705 | 8/2007 |
| JP | 2009507916 | 2/2009 |
| JP | 2010511761 | 4/2010 |
| JP | 2012508207 | 4/2012 |
| WO | WO9109586 | 7/1991 |
| WO | WO9206154 A1 | 4/1992 |
| WO | WO9213512 | 8/1992 |
| WO | WO9213512 A | 8/1992 |
| WO | WO9416680 | 8/1994 |
| WO | WO9522311 | 8/1995 |
| WO | 1876162 A | 1/1999 |
| WO | WO9902122 A1 | 1/1999 |
| WO | WO9913839 | 3/1999 |
| WO | WO9951193 | 10/1999 |
| WO | WO9962462 | 12/1999 |
| WO | WO0002981 | 1/2000 |
| WO | WO0025741 | 5/2000 |
| WO | WO0125378 | 4/2001 |
| WO | WO0246343 | 6/2002 |
| WO | WO03094874 A1 | 11/2003 |
| WO | WO03101418 A1 | 12/2003 |
| WO | WO03101418 A1 | 12/2003 |
| WO | WO2004014321 | 2/2004 |
| WO | WO2004084844 A2 | 10/2004 |
| WO | WO2005023208 | 3/2005 |
| WO | WO2005034895 | 4/2005 |
| WO | WO2005041918 A1 | 5/2005 |
| WO | 1589093 | 10/2005 |
| WO | WO2006018064 | 2/2006 |
| WO | 1639993 | 3/2006 |
| WO | 1696023 | 8/2006 |
| WO | WO2006100647 A1 | 9/2006 |
| WO | WO2007031884 A1 | 3/2007 |
| WO | WO2007040571 | 4/2007 |
| WO | WO2006063471 A3 | 3/2008 |
| WO | WO2008055815 | 5/2008 |
| WO | WO2008055816 A1 | 5/2008 |
| WO | WO2008063471 | 5/2008 |
| WO | WO2009003775 A2 | 1/2009 |
| WO | WO2009072027 | 6/2009 |
| WO | WO2009112420 | 9/2009 |
| WO | WO 2010052092 A1 * | 5/2010 |
| WO | WO2010052092 A1 | 5/2010 |
| WO | WO2010072527 A1 | 7/2010 |
| WO | WO2010149425 | 12/2010 |
| WO | WO2010149460 | 12/2010 |
| WO | WO2011092083 | 8/2011 |
| WO | WO2011117023 | 9/2011 |
| WO | WO2011120736 A1 | 10/2011 |

* cited by examiner

HAIR CARE COMPOSITION

The present invention relates to a composition giving controlled release of active materials.

WO-A-00/02981 describes reacting a perfume component with an amine to obtain a release of the active component over a longer period of time.

WO 2004/084844. describes a process for controlled release of active materials is disclosed in WO 2004/084844. This process involves the blending of the active material with cyclopentasiloxane.

There however still remains a need to improve controlled, prolonged delivery of active materials particularly fragrance from compositions containing surfactants.

Accordingly, the present invention provides a personal care composition comprising:
i) a cleaning phase comprising a cleansing anionic surfactant which is a salt and comprises an alkyl group with from 8 to 14 carbons;
ii) an aqueous conditioning gel network having no overall charge or being anionic, the gel network comprising:
   (a) fatty material;
   (b) a gel network anionic surfactant comprising an alkyl group with from 16 to 30 carbons;
   (c) cationic surfactant;
   (d) and an active material selected from fragrances, sunscreens and cooling agents
iii) a cationic deposition polymer.

The invention further relates to a method of manufacturing a hair care composition comprising the steps of
i) forming a an aqueous conditioning gel network having no overall charge or being anionic, the gel network comprising:
   (a) fatty material;
   (b) a gel network anionic surfactant comprising an alkyl group with from 16 to 30 carbons;
   (c) cationic surfactant;
   (d) an active material selected from fragrances, vitamins, sunscreens and cooling agents; and
ii) adding the resulting gel network to diluted primary surfactant solution;

Also described is a process for gradual release of an active material to the body and/or hair comprising the step of applying to the body and/or hair a composition as described above.

A further aspect is the use of a composition as described above for controlling the release of an active agent.

All viscosities mentioned in this specification are measured viscosity at 30° C. on a Brookfield viscometer with spindle RV5 and 20 rpm.

Preferably, the composition has a viscosity of 2000 to 7000 cPs measures at 30° C.

Conditioning Gel Network

The conditioning gel network comprises:
(a) fatty material;
(b) a gel network anionic surfactant comprising an alkyl group with from 16 to 30 carbons;
(c) cationic surfactant;
d) an active material selected from fragrances, pest repellents, vitamins, sunscreens and cooling agents;
wherein the conditioning gel network has no overall charge or is anionic.

The cationic surfactant provides improved robustness of the fatty material/anionic surfactant gel network leading to improved conditioning benefit from a composition also comprising a non-cationic cleansing phase. The difference in carbon chain length between the anionic surfactant in the cleansing phase and the anionic surfactant in the conditioning gel significantly improve stability of the conditioning gel network and maintain its integrity in the shampoo composition.

Preferably, the anionic and cationic surfactants in the gel network contain within 4, preferably 2 carbons and most preferably the same number of carbons. More preferably, they comprise a single alkyl group of within 4, more preferably within 2 and most preferably are the same length. This assists in maintaining stability of the gel network.

Preferably, the carbons in the gel network cationic surfactant are present in a single alkyl group. More preferably the gel network cationic surfactant has from 16 to 30 carbon groups.

Preferably, the cationic surfactants have the formula $N^+(R^1)(R^2)(R^3)(R^4)$, wherein $R^1$, $R^2$, $R^3$ and $R^4$ are independently ($C_{16}$ to $C_{30}$) alkyl or benzyl.

Preferably, one, two or three of $R^1$, $R^2$, $R^3$ and $R^4$ are independently ($C_{16}$ to $C_{30}$) alkyl and the other $R^1$, $R^2$, $R^3$ and $R^4$ group or groups are ($C_1$-$C_6$) alkyl or benzyl.

Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, stearyldimethylbenzylammonium chloride, cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Another example of a class of suitable cationic surfactants for use in the invention, either alone or in admixture with one or more other cationic conditioning surfactants, is a combination of (i) and (ii) below:
(i) an amidoamine corresponding to the general formula (I):

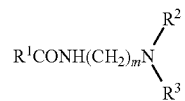

in which $R^1$ is a hydrocarbyl chain having 10 or more carbon atoms,
$R^2$ and $R^3$ are independently selected from hydrocarbyl chains of from 1 to 10 carbon atoms, and
m is an integer from 1 to about 10; and
(ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachid-amidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia Pa., USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton N.J., USA).

Acid (ii) may be any organic or mineral acid which is capable of protonating the amidoamine in the hair treatment composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate all the amidoamine present, i.e. at a level which is at least equimolar to the amount of amidoamine present in the composition.

The level of cationic surfactant will generally range from 0.01 to 10%, more preferably 0.02 to 7.5%, most preferably 0.05 to 5% by total weight of cationic surfactant based on the total weight of the composition.

The anionic surfactant of the gel network comprises an alkyl chain with from 16-30 carbons, preferably from 16-22 carbons.

Preferably, the anionic surfactant is a sulphate or sulphonate, more preferably sulphate, most preferably sodium cetylstearyl sulphate.

Preferably, the carbons in the gel network anionic surfactant are present in a single alkyl group.

The gel network comprises an anionic surfactant for achieving an overall anionic charge to the gel network or no overall charge to the gel network.

Preferably, the ratio of anionic surfactant (b) within the gel network to cationic surfactant (c) within the gel network has a ratio is from 6:1 to 20:1 most preferably 9:1 to 13:1.

The gel network comprises an anionic surfactant for achieving an overall anionic charge to the gel network or no overall charge to the gel network.

The gel network anionic surfactant is present at from 0.1 to 5% by weight of the total composition and more preferably from 0.5 to 2.0% wt.

Preferably, the fatty material is selected from fatty acids, fatty amides, fatty alcohols, fatty esters and mixtures thereof. Fatty alcohols are highly preferred.

Preferably, the fatty material comprises a fatty group having from 14 to 30 carbon atoms, more preferably 16 to 22. Examples of suitable fatty alcohols include cetyl alcohol, stearyl alcohol and mixtures thereof. An example of a suitable fatty ester is glyceryl monostearate.

The level of fatty material in compositions of the invention is conveniently from 0.01 to 10%, preferably from 0.1 to 5% by weight of the total composition.

Preferably, the ratio between fatty alcohol (a) within the gel network and anionic surfactant (b) within the gel network is from 0.1:1 to 100:1, preferably from 1.2:1 to 50:1, more preferably from 1.5:1 to 10:1 and most preferably around 2:1.

Preferably, the anionic and fatty materials of the gel network contain alkyl groups with within 4, preferably 2 carbons and most preferably the same number of carbons. More preferably, they comprise a single alkyl group of within 4, more preferably within 2 and most preferably are the same length. This assists in maintaining stability of the gel network.

Cleansing Phase

The cleaning phase comprises a cleansing surfactant. The cleansing phase anionic surfactant is a salt and has from 8 to 14 carbons, more preferably from 10 to 12 and most preferably 12 carbons. More preferably, these carbons are present in a single alkyl group.

Preferably, the salt is a sulphate, sulphonate, sarcosinate or isethionate.

Preferably, the cleansing anionic surfactant is selected from ammonium lauryl sulphate, ammonium laureth sulphate, trimethylamine lauryl sulphate, trimethylamine laureth sulphate, triethanolamine lauryl sulphate, trimethylethanolamine laureth sulphate, monoethanolamine lauryl sulphate, monoethanolamine laureth sulphate, diethanolamine lauryl sulphate, diethanolamine laureth sulphate, lauric monoglyceride sodium sulphate, sodium lauryl sulphate, sodium laureth sulphate, potassium lauryl sulphate, potassium laureth sulphate, sodium lauryl sarcosinate, sodium lauroyl sarcosinate, lauryl sarcosine, ammonium cocoyl sulphate, ammonium lauroyl sulphate, sodium cocoyl sulphate, sodium lauryl sulphate, potassium cocoyl sulphate, potassium lauryl sulphate, monoethanolamine cocoyl sulphate, monoethanolamine lauryl sulphate, sodium tridecyl benzene sulphonate, sodium dodecyl benzene sulphonate, sodium cocoyl isethionate and mixtures thereof.

Preferred anionic cleansing surfactants include alkali metal alkyl sulphates, more preferably the alkyl ether sulphates. Particularly preferred anionic cleansing surfactants include sodium lauryl ether sulphate.

The invention encompasses both regular cleansing compositions comprising typical levels of cleansing surfactant as well as concentrated compositions. In a regular composition the level of cleansing surfactant is preferably from 5 to 26% by weight of the total composition while for concentrated compositions the level of cleansing surfactant is from 27 to 70% by weight of the total composition.

Preferably, the composition comprises no fatty acid. Preferably, the composition comprises no fatty acid having from 10 to 20 carbon atoms in an alkyl chain. Fatty acids are not desirable since they provide a poor quality conditioning benefit to the hair.

Deposition Polymer

The composition according to the invention comprises a cationic deposition polymer.

Suitable cationic deposition aid polymers may be homopolymers which are cationically substituted or may be formed from two or more types of monomers. The weight average ($M_w$) molecular weight of the polymers will generally be between 100 000 and 2 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-07 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo-and copolymers of unsaturated carboxylic acids having from 3 to 5 carbon atoms, (as described in U.S. Pat. No. 4,009, 256);
cationic polyacrylamides(as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include monomers of the formula:

A-O—[R—N⁺(R¹)(R²)(R³)X⁻], wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR C14, JAGUAR C15 and JAGUAR C17.

The cationic deposition polymer may be a hydrophobically modified cationic deposition polymer having a carbon chain having from 14 to 30 carbons. It is preferred if the carbon chain is a single alkyl chain, more preferably unbranched.

The hydrophobic modified cationic polymers can comprise mixtures of monomer units derived from amine- and/or quaternary ammonium-substituted monomer and/or compatible spacer monomers.

The hydrophobically cationic deposition polymer can be obtained from hydrophobically modifying deposition polymers from the group consisting of guar, locust bean, tara gum, honey locust, cassia, fenugreek and flame tree. Others useful polymers could include xanthan gum, gellan gum, welan gum, rhamsan gum, konjac, mannan, gum Arabic, soy polysaccharide, xylofructose gums, polyglucose (starch) and tamarind gum.

Mixtures of any of the above cationic polymers may be used.

Cationic polymer will generally be present in a shampoo composition of the invention at levels of from 0.01 to 5%, preferably from 0.05 to 2%, more preferably from 0.07 to 1.2% by total weight of cationic polymer based on the total weight of the composition.

Active Materials

A preferred active material is a fragrance. The fragrance may be solid or liquid. It may and be a single fragrant compound, a natural scented oil, or a mixture of fragrant compounds and/or natural oils.. The fragrance can alternatively comprise a chemically protected fragrance compound such as a reaction product of the fragrance compound.

An alternative type of active material which can be incorporated in the controlled release composition is a sunscreen. Examples of sunscreens include those which absorb ultraviolet light between about 290-320 nanometers (the UV-B region) such as para-aminobenzoic acid derivatives and cinnamates such as octyl methoxycinnamate or 2-ethoxyethyl p-methoxycinnamate; and those which absorb ultraviolet light in the range of 320-400 nanometers (the UV-A region) such is benzophenones and butyl methoxy dibenzoylmethane. Additional examples of sunscreen chemicals which may be used as active material in the present invention include menthyl anthranilate; homomenthyl salicylate; glyceryl p-aminobenzoate; isobutyl p-aminobenzoate; isoamyl p-dimethylaminobenzoate; 2,2'-dihydroxy-4-methoxybenzophenone; 2-hydroxy-4-methoxybenzophenone; 4-mono and 4-bis(3-hydroxy-propyl)amino isomers of ethyl benzoate; and 2-ethylhexyl p-dimethylaminobenzoate. The invention is particularly applicable to lipophilic screening agents, including the family of screening agents derived from dibenzoylmethane and more especially 4-tert-butyl-4'-methoxydibenzoylmethane, which effectively have a high intrinsic power of absorption. These dibenzoylmethane derivatives are well known as UV-A active screening agents and are described in particular in European patent application EP-A-0,114,607. 4-(tert-butyl)-4'-methoxydibenzoylmethane is sold under the trade mark "Parsol 1789" by Givaudan. Another dibenzoylmethane derivative which is preferred according to the present invention is 4-isopropyldibenzoylmethane, sold under the name "Eusolex 8020" by Merck. Octocrylene, a liquid lipophilic screening agent known for its activity in the UV-B range and sold under the trade mark "Uvinul N 539" by BASF. Another lipophilic (or liposoluble) screening agent which can be used in the invention is p-methylbenzylidenecamphor, which is known as a UV-B absorber and is sold under the trade name "Eusolex 6300" by Merck. The sunscreen can alternatively be a hydrophilic screening agent, for example one or more of those described in Application EP-A-678,292, particularly a 3-benzylidine-2-camphorsulphonic derivative such as benzene-I,4-[di(3-methylidenecamphor-10-sulphonic acid)], known under the trade name Mexoryl SX, or a sulphonic derivative of benzophenone or 2-phenylbenzimidazole-5-sulphonic acid, for example that sold under the trade mark "Eusolex 232" by Merck, benzene-1,4-di(benzimidazol-2-yl-5-sulphonic acid) or benzene-1,4-di(benzoxazol-2-yl-5-sulphonic acid).

Further suitable active materials include vitamins. Some vitamins also have beneficial effects when applied topically and for this reason are popular ingredients in various personal care formulations. Vitamins comprise a variety of different organic compounds such as alcohols, acids, sterols, and quinones. They can be classified into two solubility groups: lipid-soluble vitamins and water-soluble vitamins. Lipid-soluble vitamins that have utility in personal care formulations include retinol (vitamin A), ergocalciferol (vitamin $D_2$), cholecalciferol (vitamin $D_3$), phytonadione (vitamin K), and tocopherol (vitamin E). Water-soluble vitamins that have utility in personal care formulations include ascorbic acid (vitamin C), thiamin (vitamin Bi) niacin (nicotinic acid), niacinamide (vitamin $B_3$), riboflavin (vitamin $B_2$), pantothenic acid (vitamin $B_5$), biotin, folic acid, pyridoxine (vitamin $B_6$), and cyanocobalamin (vitamin $B_{12}$).

Many of the vitamins that are used in personal care compositions are inherently unstable and therefore present difficulties in the preparation of shelf-stable personal care compositions. The instability of the vitamins is usually related to their susceptibility to oxidation. For this reason, vitamins are often converted into various derivatives that are more stable in personal care formulations. These vitamin derivatives offer other advantages in addition to improved stability. Vitamin derivatives can be more amenable to certain kinds of personal care formulations. For example a lipid-soluble vitamin can be derivatized to produce a water-soluble material that is easier to incorporate into a water-based formulation. Retinol and tocopherol are two lipid-soluble vitamins that are particularly useful in skin care compositions and consequently there are many different derivatives of these two vitamins that are used in personal care compositions. Derivatives of retinol include retinyl palmitate (vitamin A palmitate), retinyl acetate (vitamin A acetate), retinyl linoleate (vitamin A linoelate), and retinyl propionate (vitamin A propioniate). Derivatives of tocopherol include tocopheryl acetate (vitamin E acetate), tocopheryl linoleate (vitamin E linoleate), tocopheryl succinate (vitamin E succinate), tocophereth-5, tocophereth- 10, tocophereth- 12, tocophereth- 18, tocophereth-50 (ethoxlyated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin E derivatives), and sodium tocopheryl phosphate. The invention can be used to give controlled release of these vitamin derivatives. Derivatives of ascorbic acid (Vitamin C) such as ascorbyl palmitate, ascorbyl dipalmitate, ascorbyl glucoside, ascorbyl tetraisopalmitate, and tetrahexadecyl ascorbate can also be used as the active material, as can vitamin derivatives incorporating two different vitamins in the same compound, for example ascorbyl tocopheryl maleate, potassium ascorbyl tocopheryl phosphate or tocopheryl nicotinate.

The active material can also be a cooling agent (a material which gives a cooling sensation to the skin) such as menthol or other cooling agents described in W096/19119. The cooling agent can be incorporated in a composition to give prolonged release of the cooling agent.

Silicones

The hair care composition of the invention may comprises silicone. It is preferable if the silicone is present as emulsified particles. Particularly preferred are non-volatile silicones.

The term "non-volatile" as used herein means that the material in question has a vapour pressure under ambient conditions of 0.2 mm Hg or less, preferably about 0.1 mm Hg or less.

By "non-alkyl modified silicone" is generally meant an organosiloxane polymer which does not contain any pendant alkyl group having a hydrocarbyl chain length of $C_6$ or greater extending from at least one of the silicon atoms forming the polymer backbone.

Suitable non-volatile, non-alkyl modified silicones for use in the invention have a viscosity ranging from 350 to 200,000,000 $mm^2\ sec^{-1}$ at 25° C. Preferably the viscosity is at least 5,000, more preferably at least 10,000 $mm^2\ sec^{-1}$ at 25° C. Preferably the viscosity does not exceed 20,000,000, more preferably 10,000,000, most preferably 5,000,000 $mm^2\ sec^{-1}$ at 25° C.

All silicone viscosities mentioned herein are kinematic viscosities unless otherwise specified, and are generally provided by suppliers of silicones, either as measured at 25° C. using calibrated capillary glass viscometers under gravity flow conditions, or as deduced from the molecular weight of the material in question.

Preferred non-volatile, non-alkyl modified silicones for use in the invention have a number average molecular weight ($M_n$) ranging from 10,000 to 1,000,000, more preferably from 100,000 to 500,000 dalton.

Suitable non-alkyl modified silicones for use in the hair care compositions of the invention may be chemically characterised by the general formula (II):

$$A(R)_2Si-O-[Si(R)_2-O]_x-Si(R)_2A \qquad (II)$$

in which each R is independently selected from $C_{1-4}$ alkyl or aryl, x is an integer from 200 to 8,000 and each A is independently selected from $C_{1-4}$ alkyl, $C_{1-4}$ alkoxy, aryl, aryloxy or hydroxyl.

In preferred materials of general formula (II) for use in the invention, all R groups are methyl and both A groups are either methyl or hydroxyl. Such materials have the CTFA designation "dimethicone" and "dimethiconol" respectively. Most preferably, all R groups are methyl and both A groups are hydroxyl.

Also suitable as non-volatile, non-alkyl modified silicones for use in the hair care compositions of the invention are aminofunctional polydimethylsiloxanes having the CTFA designation "amodimethicone", and the general formula (III):

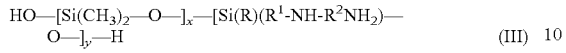

in which R is $CH_3$ or OH, x and y are independent integers of 1 or more and $R^1$ and $R^2$ are each independently an alkylene group having from 2 to 5 carbon atoms.

Also suitable as non-volatile, non-alkyl modified silicones for use in the hair care compositions of the invention are aminofunctional polydimethylsiloxanes having the CTFA designation "trimethylsilylamodimethicone", and the general formula (IV):

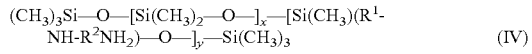

in which x and y are independent integers of 1 or more and $R^1$ and $R^2$ are each independently an alkylene group having from 2 to 5 carbon atoms.

Mixtures of any of the above described non-volatile, non-alkyl modified silicones may also be used.

The non-volatile, non-alkyl modified silicone is present as emulsified particles in the hair care composition of the invention.

The emulsified particles of non-volatile, non-alkyl modified silicone may typically have a Sauter mean particle diameter ($D_{3,2}$) in the composition of the invention ranging from 0.01 to 10, preferably from 0.1 to 5, more preferably from 0.5 to 2.5 micrometres.

Non-volatile, non-alkyl modified silicones for use in compositions of the invention are available as pre-formed silicone emulsions from suppliers of silicones such as those mentioned above. The use of such pre-formed silicone emulsions is preferred for ease of processing and control of silicone particle size. Such pre-formed silicone emulsions will typically additionally comprise a suitable emulsifier, such as an anionic or non-ionic surfactant, and may be prepared by a chemical emulsification process such as emulsion polymerisation, or by mechanical emulsification using a high shear mixer.

Examples of suitable commercially available pre-formed emulsions are Dow Corning® 1784 Emulsion and Dow Corning® 1785 Emulsion. These are both anionic emulsions of dimethiconol.

The total amount of non-volatile, non-alkyl modified silicone in hair care compositions of the invention generally ranges from 0.1 to 10%, preferably from 0.5 to 5%, more preferably from 1 to 3% by total weight non-volatile, non-alkyl modified silicone based on the total weight of the composition.

In the composition of the invention, the weight ratio of alkyl modified silicone (as defined above) to non-volatile, non-alkyl modified silicone (as defined above) generally ranges from 10:1 to 1:10, preferably from 1:1 to 1:10, more preferably from 1:2 to 1:8.

Solvent

Preferably, the hair care compositions of the invention are aqueous, i.e. they have water or an aqueous solution or a lyotropic liquid crystalline phase as their major component.

Suitably, the composition will comprise from 10 to 98%, preferably from 30 to 95% water by weight based on the total weight of the composition.

Optionally, a composition of the invention may contain further ingredients as described below to enhance performance and/or consumer acceptability.

The composition can include co-surfactants, to help impart aesthetic, physical or cleansing properties to the composition.

An example of a co-surfactant is a nonionic surfactant, which can be included in an amount ranging from 0.5 to 10%, preferably from 0.7 to 6% by weight based on the total weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide. A particularly preferred nonionic surfactant is coco mono-ethanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

A preferred example of a co-surfactant is an amphoteric or zwitterionic surfactant, which can be included in an amount ranging from 0.5 to about 10%, preferably from 1 to 6% by weight based on the total weight of the composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

The total amount of surfactant (including any co-surfactant, and/or any emulsifier) in a shampoo composition of the invention is generally from 1 to 70%, preferably from 2 to 65%, more preferably from 8 to 60% by total weight surfactant based on the total weight of the composition.

Suspending Agent

Preferably, an aqueous shampoo composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent will generally be present in a shampoo composition of the invention at levels of from 0.1 to 10%, preferably from 0.5 to 6%, more preferably from 0.9 to 4% by total weight of suspending agent based on the total weight of the composition.

Preferably, the composition has a viscosity of 2000 to 7000 cPs measures at 30° C., measured on a Brookfield Viscometer using spindle RV5 at 20 rpm.

Oil

The composition preferably may comprises an oil. The oil may be any oil commonly used in personal care products for example polyolefin oils, ester oils, triglyceride oils, hydrocarbon oils and mixtures thereof. Preferably, the oil is a light oil. Oils, enhance the conditioning benefits found with compositions of the invention.

Preferred oils include those selected from:
Oils having viscosities from 0.1 to 500 centipoises measures at 30° C.
Oils with viscosity above 500 centipoises (500-500000 cps) which contains up to 20% of a lower viscosity fraction (less than 500cps).
One type of preferred oil is a polyalphaolefin oil.

Suitable polyalphaolefin oils include those derived from 1-alkalene monomers having from 6 to 16 carbons, preferably from 6 to 12 carbons. Non limiting examples of materials include 1-hexene, 1-octene, 1-decene, 1-dodecene, 1-tetradecene, 1-hexadecene, branched isomers such as 4-methyl-1-pentene and mixtures thereof.

Preferred polyalphaloefins include polydecenes with tradename Puresyn 6 having a number average molecular weight of about 500, Puresyn 100 having a molecular weight of about 3000 and Puresyn 300 having a molecular weight of about 6000 commercially available from Mobil.

Preferably, the polyalphaolefin oil is present at from 0.05 to 10%, particularly from 0.2 to 5%, and especially from 0.5 to 3% by weight of the composition.

Also suitable are triglyceride oils include fats and oils including natural fats and oils such as jojoba, soybean, sunflower seed oil, rice bran, avocado, almond, olive, sesame, castor, coconut, coconut palm oil, sunflower oil, mink oils; cacao fat; beef tallow, lard; hardened oils obtained by hydrogenating the aforementioned oils; and synthetic mono, di- and triglycerides such as myristic acid glyceride and 2-ethylhexanoic acid glyceride.

Preferably, the triglyceride oil if present is at levels from 0.05 to 10%, particularly from 0.2 to 5%, and especially from 0.5 to 3% by weight of the composition. Highly suitable oils for use with the present invention are hydrocarbon oils. Hydrocarbon oils have at least 12 carbon atoms, and include paraffin oil, polyolefin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Also suitable are polymeric hydrocarbons of $C_{2-6}$ alkenyl monomers, such as polyisobutylene.

Preferably, the hydrocarbon oil is present at from 0.05 to 10%, particularly from 0.2 to 5%, and especially from 0.5 to 3% by weight of the composition.

Also suitable are ester oils which have at least 10 carbon atoms, and include esters with hydrocarbyl chains derived from fatty acids or alcohols. Typical ester oils are formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Preferably, the ester oil is present at from 0.05 to 10%, particularly from 0.2 to 5%, and especially from 0.5 to 3% by weight of the composition.

Preferably, the composition comprises a cleansing anionic surfactant which comprises an alkyl group with from 10 to 14 carbons.

A further component that may be used in compositions of the invention is a hydrocarbon oil or ester oil. Like silicone oils, these materials may enhance the conditioning benefits found with compositions of the invention.

Suitable hydrocarbon oils have at least 12 carbon atoms, and include paraffin oil, polyolefin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Also suitable are polymeric hydrocarbons of $C_{2-6}$ alkenyl monomers, such as polyisobutylene.

Suitable ester oils have at least 10 carbon atoms, and include esters with hydrocarbyl chains derived from fatty acids or alcohols. Typical ester oils are formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Mixtures of any of the above described hydrocarbon/ester oils also be used.

The total combined amount of hydrocarbon oil and ester oil in compositions of the invention may suitably range from 0.05 to 10%, particularly from 0.2 to 5%, and especially from 0.5 to 3% by weight of the composition.

Other Ingredients

A composition of the invention may contain other ingredients for enhancing performance and/or consumer acceptability. Such ingredients include fragrance, dyes and pigments, pH adjusting agents, pearlescers or opacifiers, viscosity modifiers, and preservatives or antimicrobials. Each of these ingredients will be present in an amount effective to accomplish its purpose. Generally these optional ingredients are included individually at a level of up to 5% by weight of the total composition.

Method of Manufacture

Water, preferably at least 7 wt % of the total composition was heated to 80° C. or above. To this, was added cationic surfactant (Behenyl Trimethyl Ammonium Chloride), fatty alcohol, secondary anionic surfactant (Sodium Cetylstearyl sulphate) and perfume using high speed stirring. When uniform dispersion obtained, this mixture was cooled down to about 45° C. or below with the same speed stirring. This mixture was then added in the diluted primary surfactant solution (Sodium Laureth Sulphate) following by remaining components with moderate speed stirring.

In a second embodiment the perfume can also be added before the secondary anionic surfactant.

Mode of Use

The compositions of the invention are primarily intended for topical application to the body, preferably the hair and/or scalp of a human subject in rinse-off compositions.

The compositions provided by the invention are preferably shampoo compositions for the treatment of hair (typically after shampooing) and subsequent rinsing.

Alternatively the compositions provided by the invention may be aqueous conditioner compositions, used by massaging them into the hair followed by rinsing with clean water prior to drying the hair.

The invention will be further illustrated by the following, non-limiting Example, in which all percentages quoted are by weight based on total weight unless otherwise stated.

EXAMPLES

The following are example according to the invention

| Component | % ad | 1 | 2 |
|---|---|---|---|
| Sodium Laureth Sulphate | 70 | 17.14 | 17.14 |
| Cocoamidopropyl Betaine | 30 | 5.33 | 5.33 |
| Carbomer | 100 | 0.4 | 0.4 |
| Glycol Distearate | 35 | 4.0 | 4.0 |
| Dimethiconol | 50 | 4.0 | 4.0 |
| Sodium Cetylstearyl sulphate | 100 | 0.6 | 0.6 |
| Cetostearyl Alcohol | 100 | 1.0 | 1.0 |
| Cetyl trimethylammonium chloride | 29 | — | 0.17 |
| Behenyl Trimethyl Ammonium Chloride | 77.5 | 0.06 | — |
| Guar Hydroxypropyl Trimonium Chloride | 100 | 0.2 | 0.2 |
| Perfume | 100% | 0.8 | 0.8 |
| DMDM Hydantoin and 3-iodo-2propylnylbutyl carbamate | 50% | 0.2 | 0.2 |
| Sodium chloride | 100% | Visc. | Visc. |
| Aqua | | q.s. to 100 | q.s. to 100 |

Process

At least 7% of water was heated to about 80° C. in a side pot. To this, was added cationic surfactant (Behenyl Trimethyl Ammonium Chloride), fatty alcohol, secondary anionic surfactant (Sodium Cetylstearyl sulphate) and perfume using high speed stirring. When uniform dispersion obtained, this mixture was cooled down to about 45° C. with the same speed stirring. This mixture was then added in the diluted primary surfactant solution (Sodium Laureth Sulphate) following by remaining components with moderate speed stirring.

To demonstrate the advantage of adding the perfume to the gel phase the Examples of table 2 were prepared:

TABLE 2

| Component | % ad | Example A/ perfume added outside gel | Example 1/ perfume added inside gel | Example 3/ perfume inside gel |
|---|---|---|---|---|
| Sodium Laureth Sulphate | 70 | 17.14 | 17.14 | 17.14 |
| Cocoamidopropyl Betaine | 30 | 5.33 | 5.33 | 5.33 |
| Carbomer | 100 | 0.4 | 0.4 | 0.4 |
| Glycol Distearate | 35 | 4 | 4 | 4 |
| Dimethiconol | 50 | 4 | 4 | 4 |
| Sodium Cetylstearyl sulphate | 100 | 0.6 | 0.6 | 0.6 |
| Cetostearyl Alcohol | 100 | 1 | 1 | 1 |
| Behenyl Trimethyl Ammonium Chloride | 77.5 | 0.06 | 0.06 | 0.06 |
| Guar Hydroxypropyl Trimonium Chloride | 100 | 0.2 | 0.2 | 0.2 |
| Perfume | 100% | 0.8 | 0.8 | 0.1 |
| DMDM Hydantoin and 3-iodo-2propylnylbutyl carbamate | 50% | 0.2 | 0.2 | 0.2 |
| Sodium chloride | 100% | Visc. | Visc. | Visc. |
| Aqua | | q.s. to 100 | q.s. to 100 | q.s. to 100 |

Example 1 and 3 were prepared as described above.

Examples A was prepared using a similar method, however the perfume was not added to the anionic/cationic gel phase but to the diluted primary surfactant solution (Sodium Laureth Sulphate).

The resulting product was placed on the hair and assessed by a trained panel of assessors. The experiment was repeated three time and the scores averaged.

TABLE 3

| Example 1 versus Example A | | |
|---|---|---|
| | % Votes (Fragrance encapsulated in Gel) Example 1 | % Votes (Free fragrance outside of gel) Example A |
| Fresh | 46.67 | 53.33 |
| 2 hrs | 60.00 | 40.00 |
| 4 hrs | 46.81 | 53.19 |
| 24 hrs | 58.97 | 41.03 |
| 25 hrs/comb | 73.81 | 26.19 |

TABLE 4

| | Example 3 versus Example A | |
|---|---|---|
| Sample | % Votes (Fragrance encapsulated in gel) Example 3 | % Votes (Free fragrance outside of gel) Example A |
| 2 hrs | 2.44 | 97.56 |
| 4 hrs | 19.51 | 80.49 |
| 24 hrs | 30.77 | 69.23 |
| 25 hrs/comb | 71.79 | 28.21 |

The above Examples demonstrate that the gel is able to encapsulate the fragrance. This slowly releases over time and is able to deliver a burst of fragrance on combing after 25 hours. The free fragrance does not deliver this burst and the perfume is mostly released early on in drying process.

The invention claimed is:

1. A method of manufacturing a hair care composition comprising the steps of
   i) forming an aqueous conditioning gel network which has no overall charge or is anionic, the gel network comprising:
      (a) fatty material;
      (b) a gel network anionic surfactant comprising an alkyl group with from 16 to 30 carbons;
      (c) cationic surfactant;
      (d) an active material selected from the group consisting of fragrances, pest repellents, vitamins, sunscreens and cooling agents and mixtures thereof; and
   ii) adding the resulting gel network to diluted primary surfactant solution
   wherein the fatty material is selected from a group consisting of fatty alcohols, fatty esters, fatty acids, and fatty amides, having straight chain or branched, and having from 14 to 30 carbons,
   wherein the ratio between (a) and (b) within the conditioning gel network is from 1.2:1 to 50:1, and
   wherein the ratio between (b) and (c) within the conditioning gel network is from 9:1 to 13:1.

2. A method according to claim 1 wherein the gel network anionic surfactant has from 16 to 22 carbons.

3. A method according to claim 1 wherein the gel network cationic surfactant has from 16 to 30 carbons.

4. A method according to claim 1 in which the active material is a fragrance.

5. A method according to claim 1 in which the composition further comprises a suspending agent.

6. A method according to claim 1 wherein the composition further comprises a cleansing anionic surfactant which is a sulphate, sulphonate, sarcosinate or isethionate.

7. A method as described in claim 1 in which the composition further comprises a cationic deposition polymer.

8. A process for gradual release of an active material to the body and/or hair comprising the step of applying to the body and/or hair a composition as described in claim 1.

* * * * *